United States Patent [19]
Brynjestad

[11] Patent Number: 5,908,383
[45] Date of Patent: Jun. 1, 1999

[54] KNOWLEDGE-BASED EXPERT INTERACTIVE SYSTEM FOR PAIN

[76] Inventor: Ulf Brynjestad, 1926 Rancho Andrew, Alpine, Calif. 91901

[21] Appl. No.: 08/932,256

[22] Filed: Sep. 17, 1997

[51] Int. Cl.$^6$ ....................................................... A61N 5/00
[52] U.S. Cl. ............................ 600/300; 600/301; 128/920
[58] Field of Search .................................... 600/300–301; 128/920, 923, 924, 925, 898

[56] References Cited

U.S. PATENT DOCUMENTS

| | | |
|---|---|---|
| 3,934,226 | 1/1976 | Stone et al. . |
| 4,290,114 | 9/1981 | Sinay ........................................ 128/920 |
| 5,299,121 | 3/1994 | Brill et al. ............................... 128/920 |
| 5,583,201 | 12/1996 | Cameron, Sr. et al. . |
| 5,619,991 | 4/1997 | Sloane ...................................... 600/300 |
| 5,658,250 | 8/1997 | Blomquist et al. . |
| 5,672,154 | 9/1997 | Sillen et al. ............................. 128/924 |
| 5,769,074 | 6/1998 | Barnhil et al. ........................... 128/924 |
| 5,772,585 | 6/1998 | Lavin et al. .............................. 128/920 |

*Primary Examiner*—Robert L. Nasser
*Assistant Examiner*—Michael Astorino
*Attorney, Agent, or Firm*—Fish & Richardson P.C.

[57] ABSTRACT

A computer-implemented Pain Management Advisor (PMA) based on an interactive knowledge-based expert system. The PMA facilitates the diagnosis and treatment of acute and chronic pain. The PMA system includes three key components: a knowledge-based component for use by the primary care providers; an inductive learning component and case-based reasoning technology for use by the chronic pain patient; and a third component used by primary care providers to consult with pain specialists and to update/modify pain management algorithms. One embodiment includes the steps of: (1) inputting demographic information for a patient into a computer; (2) inputting medical symptom information for the patient into the computer; (3) inputting a pain score into the computer; (4) generating a treatment plan for the patient by the steps of: automatically presenting to a care provider at least one rule-based pain management algorithm based on the demographic and medical symptom information; permitting a care provider to select one of the rule-based pain management algorithms; applying the selected rule-based algorithm to ask the patient questions about pain characteristics of the patient; inputting responses from the patient to such questions into the computer; generating a treatment plan recommendation for the patient based on the responses; (5) permitting a care provider to adopt the treatment plan; (6) generating a prescription and related instructions in accordance with the adopted treatment plan; (7) recording the adopted treatment plan and generated prescription information in the computer as a patient file.

16 Claims, 7 Drawing Sheets

KNOWLEDGE-BASED EXPERT INTERACTIVE SYSTEM FOR PAIN

TECHNICAL FIELD

This invention relates to computerized systems for medical care, and more particularly to a computer-implemented pain management advisory system.

BACKGROUND

Pain is sometimes defined as an unpleasant sensory and emotional experience associated with actual or potential tissue damage, or described in terms of such damage. The diagnosis and treatment of pain is time consuming and difficult. More than 80 million Americans suffer from chronic pain, and the cost to society of treating pain and the consequences of pain is staggering.

Very little training in the management of chronic pain is provided by medical schools. Despite such lack of formal training programs, pain management is emerging as an important medical specialty. However, while pain management specialists now exist, pain management expertise is not generally available to general practitioners. Yet according to the American Academy of Pain Management, pain specialists spend more than half of their time on therapy that would be better performed by primary care physicians. In this age of constantly escalating health care costs, it is important to increase the competency of health care providers. The most cost-effective way of doing this is not to send health care workers back to school, but to provide them with better tools to do their work.

Most physician are faced with the daily challenge of treating acute and chronic pain. The difficulties of managing chronic pain can lead to both physician and patient frustration. One of the most severe impediments to pain management is the problem of patient noncompliance with physician instructions. Even when well-designed treatment plans are followed, pain patients frequently return to their physician unsatisfied with their treatment effectiveness, or take it upon themselves to reduce their compliance with a prescribed treatment because of adverse side-effects. While such side-effects are often amenable to simple drug titration, such titration may be delayed or not even occur because care providers are too busy to provide close patient follow-up. Out of communication with a care provider, the pain patient may prematurely discontinue or otherwise modify therapy. All too often the patient returns for a follow-up visit with a prescribed treatment plan not having received a fair trial, resulting in precious time wasted.

Accordingly, the inventor has determined that there is a need for providing pain management tools to primary care physicians that also provide feedback about patient compliance. It would also be desirable if the pain management tools provide for adjusting prescribed treatment plans based on patient response. The present invention provides such tools.

SUMMARY

The invention includes a computer-implemented Pain Management Advisor (PMA) based on an interactive knowledge-based expert system which incorporates the wisdom and experience of top pain management specialists. The PMA facilitates the diagnosis and treatment of both acute (e.g., accident victims, post-surgery patients, sickle cell) and chronic (e.g., cancer, arthritis, etc.) pain. The PMA system permits inclusion of the latest knowledge regarding elicitation of relevant signs and symptoms of pain and its associated processes, accurate and complete diagnosis of the cause of pain, selection of optimum pain relief methods including alternatives, risks and benefits, options for the relief and treatment of underlying causes or secondary processes, and diagnosis and treatment of treatment side-effects.

Knowledge-based expert systems are computer programs which process an expert knowledge base, are able to make rational decisions by inferring from this knowledge, and can justify their decisions. Thus, these types of programs can process and apply human knowledge, enabling that knowledge to be used flexibly, often mimicking the outcome of a human decision-making process.

In the preferred embodiment, the PMA system includes three key components: a knowledge-based component for use by the primary care providers; an inductive learning component and case-based reasoning technology for use by the chronic pain patient; and a third component used by primary care providers to consult electronically with pain specialists, and which also is used to update/modify pain management algorithms. On the patient side the PMA system allows patients to be responsible for their own therapy, and addresses the non-compliance problem through reminder and registration functions and alarms. The PMA system also analyzes and recommends solutions to the problem of patient drug-adverse events.

One aspect of the invention includes a method for pain management comprising the steps of: (1) gathering demographic information for a patient and inputting such demographic information into a computer; (2) gathering medical symptom information for the patient and inputting such medical symptom information into the computer; (3) obtaining a pain score from the patient and inputting the pain score into the computer; (4) generating a treatment plan for the patient by the steps of: automatically presenting to a care provider at least one rule-based pain management algorithm based on the gathered demographic information and medical symptom information; permitting a care provider to select one of the rule-based pain management algorithms; applying the selected rule-based algorithm to ask the patient questions about pain characteristics of the patient; inputting responses from the patient to such questions into the computer; generating a treatment plan recommendation for the patient based on the responses, (5) permitting a care provider to adopt the treatment plan; (6) generating a prescription and related instructions in accordance with the adopted treatment plan; (7) recording the adopted treatment plan and generated prescription information in the computer as a patient file.

The PMA system reduces the cost of pain management in four ways: decreased number of physician interactions; fewer unscheduled emergency room visits; reduced number of specialist out-referrals; and more rational drug utilization for pain management.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference numbers and designations in the various drawings indicate like elements.

DETAILED DESCRIPTION

The invention includes a computer-implemented Pain Management Advisor (PMA) based on an interactive knowledge-based expert system which incorporates the wisdom and experience of top pain management specialists. The PMA facilitates the diagnosis and treatment of both acute (e.g., accident victims, post-surgery patients, sickle cell) and chronic (e.g., cancer, arthritis, etc.) pain. The PMA system permits inclusion of the latest knowledge regarding elicitation of relevant signs and symptoms of pain and its associated processes, accurate and complete diagnosis of the cause of pain, selection of optimum pain relief methods including alternatives, risks and benefits, options for the relief and treatment of underlying causes or secondary processes, and diagnosis and treatment of treatment side-effects.

Knowledge-based expert systems are computer programs which process an expert knowledge base, are able to make rational decisions by inferring from this knowledge, and can justify their decisions. In a knowledge-based system, problems are not expressed as algorithms. Instead, they are expressed as an inference decision tree. Unlike software programs, knowledge-based systems typically separate the knowledge base from the inference engine. It is the inference engine that applies the knowledge to solve the problem. These types of programs can process and apply human knowledge, enabling that knowledge to be used flexibly, often mimicking the outcome of a human decision-making process.

The Pain Management Advisory (PMA) system includes three key components: one component used by the primary care provider; a second for the use by the chronic pain patient; and a third component used by primary care providers to consult electronically with pain specialists, and which also is used to update/modify pain management algorithms.

Figure 1:
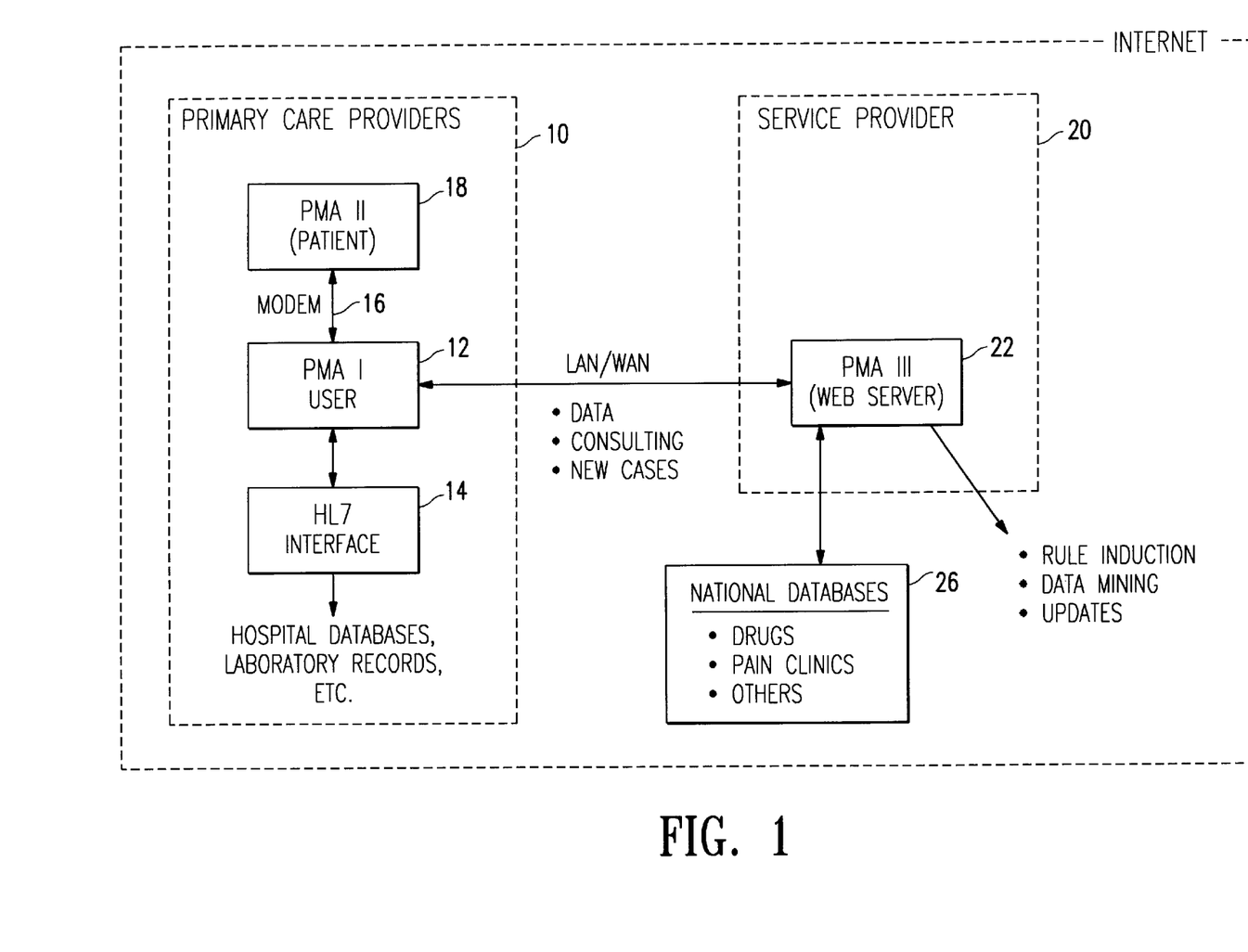
FIG. 1 is a block diagram of the basic architecture of the preferred embodiment of the invention.

FIG. 1 is a block diagram of the basic architecture of the preferred embodiment of the invention. A primary care provider environment 10 includes a PMA I knowledge-based program 12 for the use of a primary care provider. In the illustrated embodiment, the PMA I program 12 is hosted, for example, on a standard personal computer system running the Windows 95™ operating system or on a network server running under the Windows NT™ operating system. One or more user workstations capable of running the PMA I program 12 can be attached to a local area network (LAN) or a wide area network (WAN) to access and share information. A printer is required for the printout of patient instructions and prescriptions.

The PMA I program 12 preferably includes a graphical user interface for ease of use, and a medical industry-standard interface 14, such as the HL-7 interface, to permit access to other hospital or clinical databases. The PMA I program 12 also includes an interface 16, which may be, for example, a modem, to communicate with portable computers running a PMA II patient program 18. More particularly, the PMA II patient program 18 preferably is hosted on a "palmtop" computer running under the Windows CE™ operating system. The portable computer preferably is equipped with a touch-screen for patient data input, and is equipped with a conventional modem for communicating data with the PMA I program 12 (for example, to receive physician-initiated changes of patient instructions).

In a service provider environment 20, a PMA III program 22 permits a primary care provider to use the PMA I program 12 to consult electronically with pain specialists, update existing and obtain new pain management knowledge base data files, submit case feedback to the service provider to permit pain management algorithm updates and refinements, or submit new therapies not covered in the PMA I program 12. The PMA III program 22 also provides a graphical user interface for ease of use, and contains a data mining inference engine that evaluates therapies, drugs and outcomes in order to update and modify the pain management algorithms based on the experience of the primary care providers. Optionally, the PMA III program 22 may permit web-access to national databases 26 in order to gain access to the latest information on drugs, share information with pain clinics, etc. In the illustrated embodiment, the PMA III program 22 is hosted on a web server running under the Windows NT™ operating system and is accessed via the Internet™.

Figure 2:
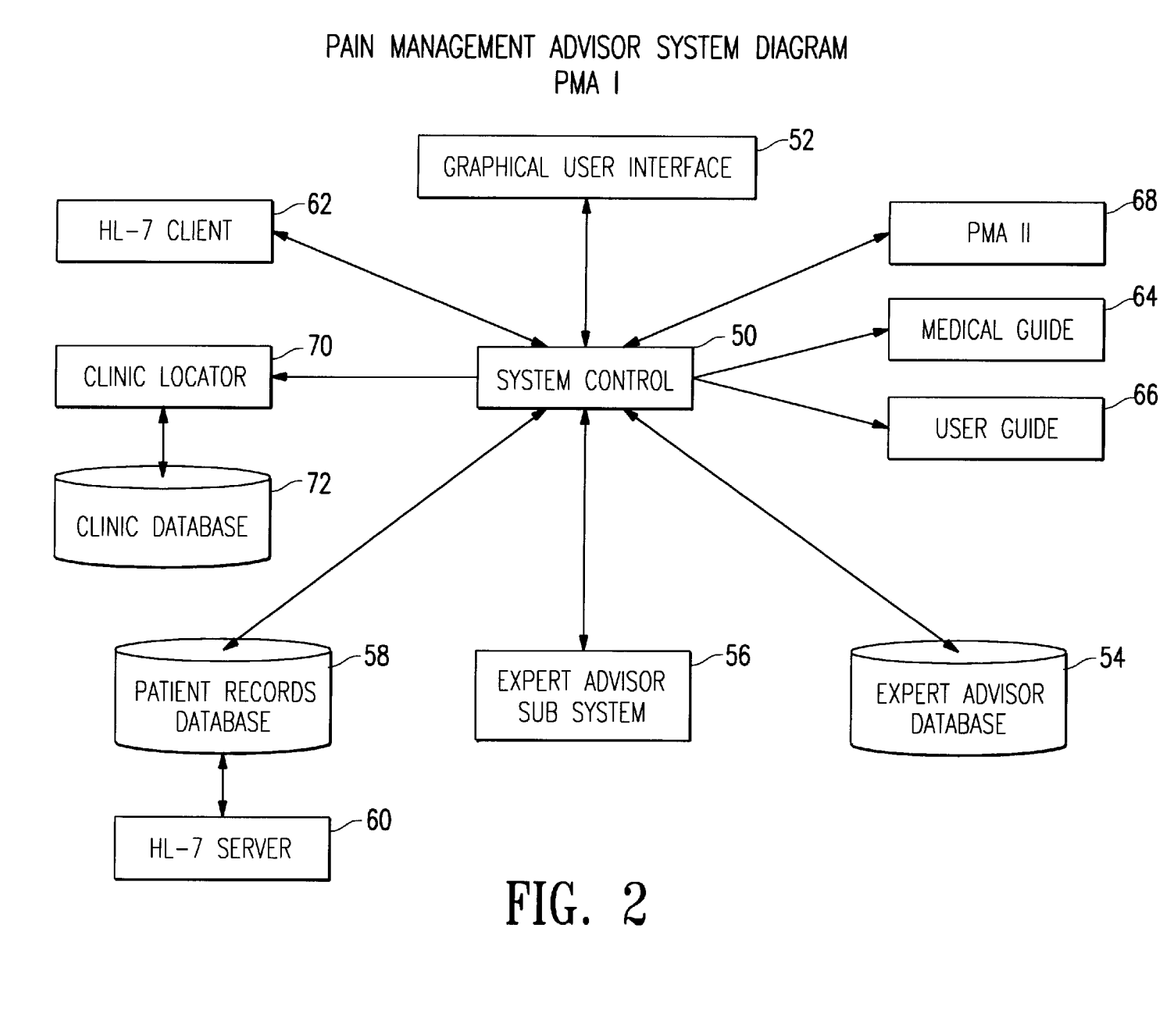
FIG. 2 is a block diagram showing the basic architecture of a preferred embodiment of the PMA I program.

FIG. 2 is a block diagram showing the basic architecture of a preferred embodiment of the PMA I program 12. A central system control module 50 acts to coordinate access to and from various databases. A graphical user interface module 52 provides a user-friendly graphical display and input interface to the PMA I program 12. The graphical user interface module 52 may provide, for example, a basic Windows95-type interface. The system control module 50 further provides access methods to an expert advisor database 54, which contains pain management rules, and an expert advisor subsystem 56, which includes an inference engine that applies the pain management rules to a particular patient. The PMA system utilizes one or more relational databases to capture a knowledge base of pain management rules, and an inference engine for applying those rules to diagnose and recommend therapy for chronic pain. In the preferred embodiment, the PMA I program 12 is based upon the XpertRule inference engine available from Attar Software of the United Kingdom. In one actual embodiment, the PMA system employs a knowledge base rule set derived from the expertise of renowned pain management specialists with many years' clinical experience.

The system control module 50 also provides access methods to a patient records database 58, as well as to a medical industry-standard HL-7 interface server database 60. The system control module 50 may also include a medical industry-standard HL-7 interface client interface 62. Help files, such as a medical guide 64 and user guide 66, may be accessed by means of the system control module 50, which may also include a PMA II interface module 68. A clinic locator module 70 may provide a directory for a number of accessible clinic databases 72.

Figure 3:
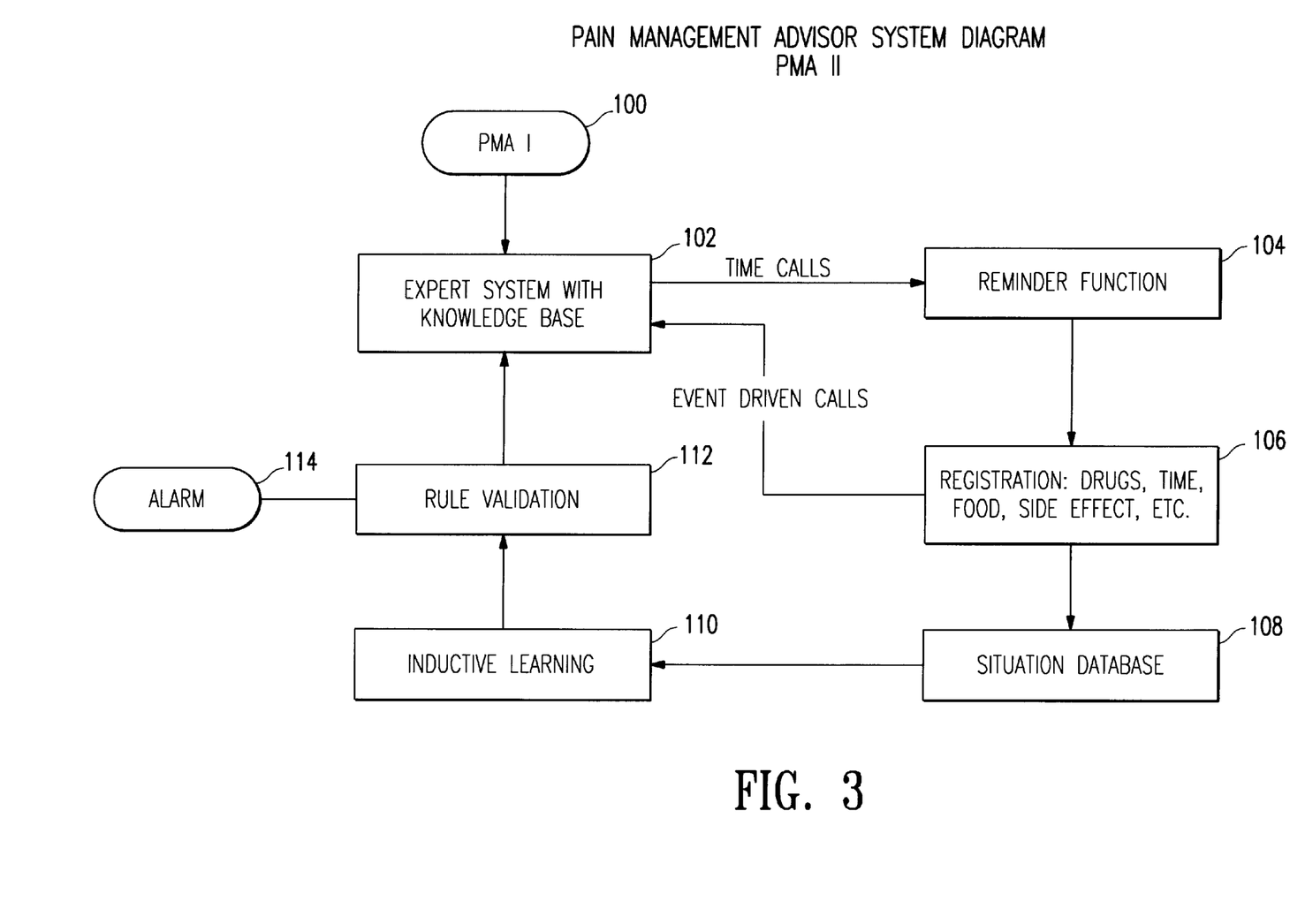
FIG. 3 is a block diagram showing the basic architecture of a preferred embodiment of the PMA II program.

FIG. 3 is a block diagram showing the basic architecture of a preferred embodiment of the PMA II program 18. The PMA II program 18 includes an interface module 100 through which it may communicate with the PMA I program 12. An expert system 102 accepts an initial set of instructions from the primary care provider, including a knowledge base applicable to a particular patient. Through a reminder function 104 and a registration function 106, the PMA II program 18 collects patient data such as general health, whether and when medication was taken, other physical or mentally stressing activities, and observed side effects from medication or activities. Such data is stored in a situation database 108. An inductive learning module 110 uses the data stored in a situation database 108 along with inductive learning and case-based reasoning to generate new rules for the management of a particular type of pain. A rule validation module 112 compares each new rule with guidelines established by the primary care provider. As long as the new rules do not violate the guidelines established by the primary care provider they are implemented. If a new rule violates these guidelines, an alarm 114 instructs the patient to download the data to the clinic and receive new instructions.

Figure 4A:
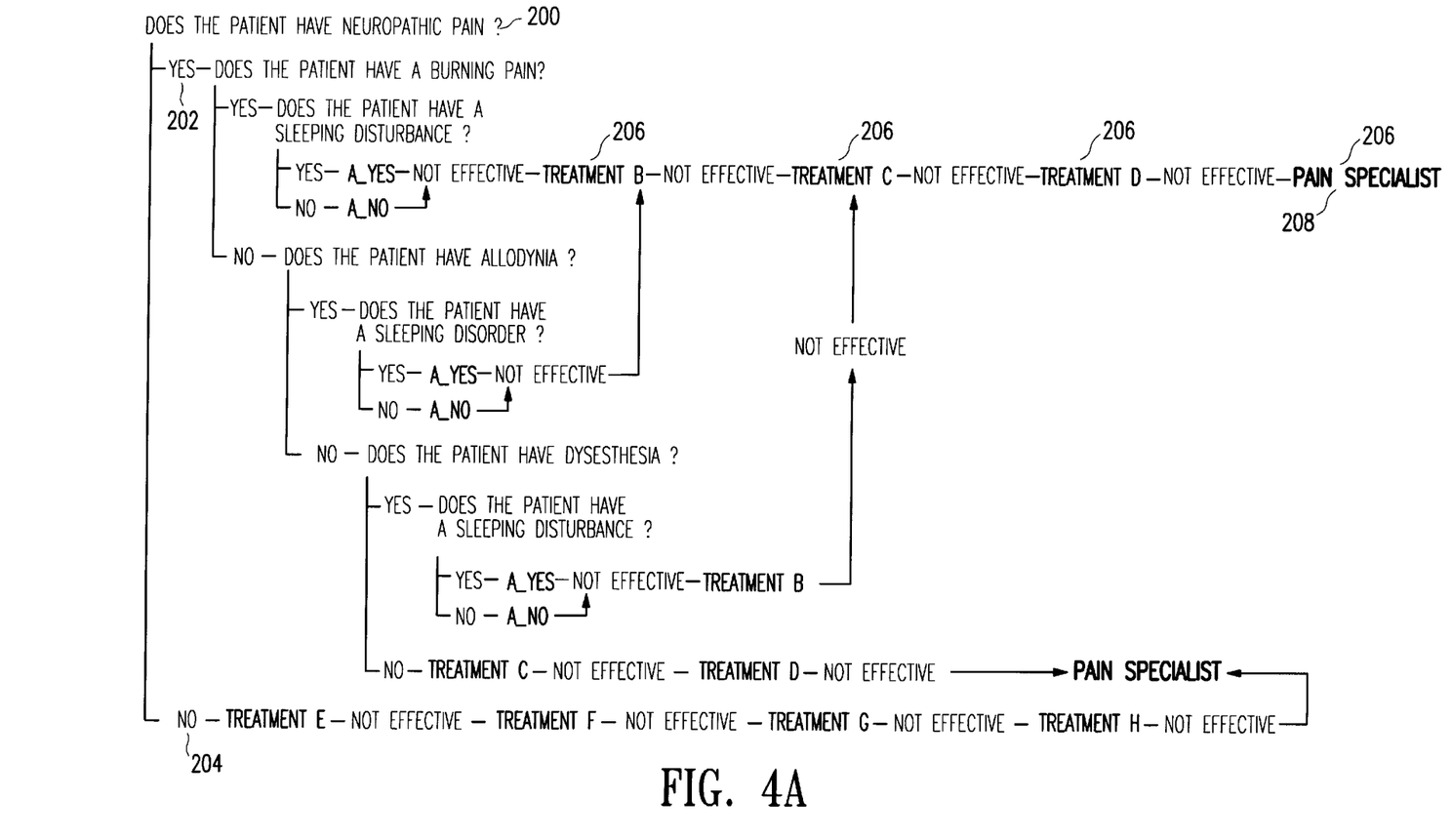
FIGS. 4A, 4B, and 4C are examples of the structure and content of several pain management algorithms that may be used with the present invention.
Figure 4B:
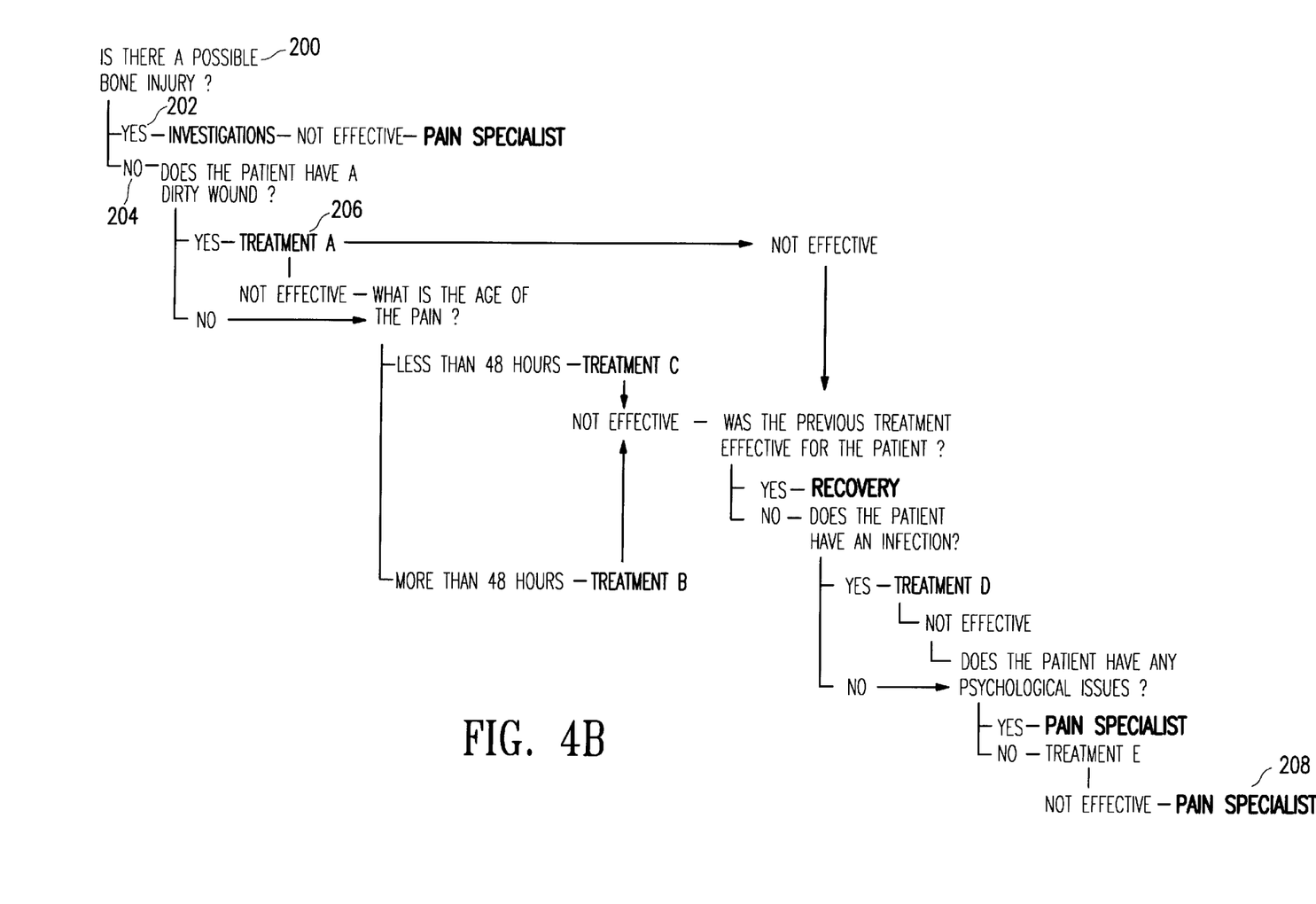
Figure 4C:
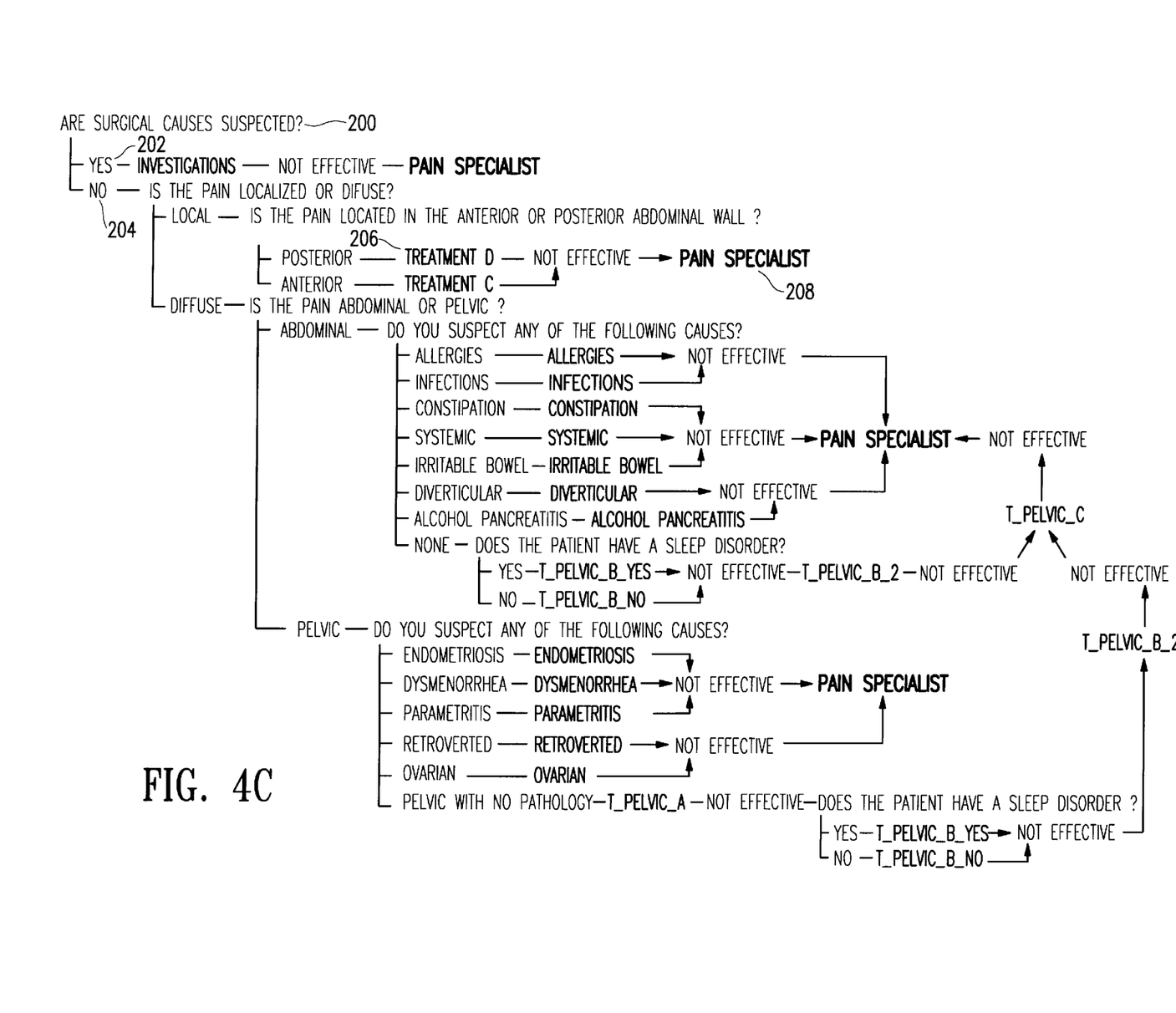

FIGS. 4A, 4B, and 4C are examples of the structure and content of several pain management algorithms that may be used with the present invention. Each algorithm shows a set of questions, starting with an initial question 200, that would be presented to the patient by means of an inference engine. The first level branches 202, 204 lead to additional questions to pose, or to one or more inferences and recommendations 206 (which may include directing the patient to a pain specialist 208), depending on the patient's response to prior questions. The system is designed so that the contents of any particular treatment can be changed independently of the line of questions that lead to the treatement.

Each such pain management algorithm may be based upon the views and experience of experts in the field, correlating clinical recognition of cause and effect. Such information may be gleaned from standard texts, such as "Pain Management for the Practicing Physician" edited by G. Irving and M. Wallace (Churchill Livingstone 1997), or be obtained by questioning clinical practitioners. Such rules may also be inductively determined by statistical analysis of clinical data, such as by observing a correlation in clinical data that administration of a particular drug is more effective in adults than in children.

Figure 5:
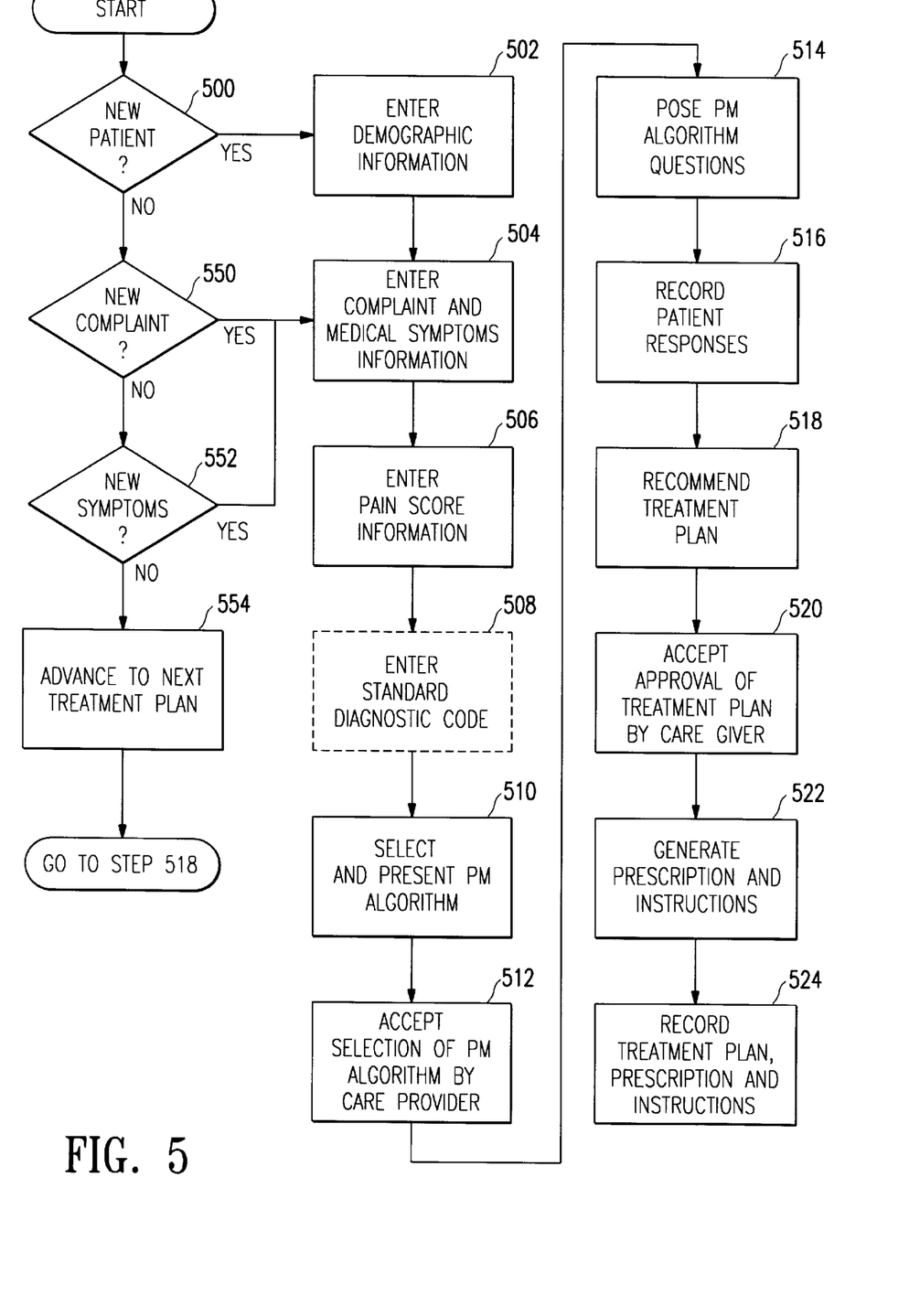
FIG. 5 is a flowchart showing the operation of a preferred embodiment of the invention.

FIG. 5 is a flowchart showing the operation of a preferred embodiment of the invention. When a patient arrives at a primary care provider, an initial determination is made as to whether the patient is new or is already enrolled (STEP 500). In the case of a new patient, demographic data (e.g., sex, age, race, medical history, etc.) is collected and entered into a patient database (STEP 502). Such information may be gathered by presenting suitable graphical user interface screens to the patient and permitting the patient to fill in blank items, or by having a care provider ask questions orally and record oral answers. Similarly, information about the patient's basic complaint (e.g., head pain, chest pain, etc.) and medical symptoms (e.g., fever, dizziness, difficulty eating or breathing, etc.) is collected and entered into the patient database (STEP 504).

The patient's initial "pain score" is recorded, typically on a 1 to 10 scale (STEP 506). It has been found from experience that the patient's subjective ranking of his or her pain is one of the best indicators of actual pain severity.

Optionally, a standard diagnostic classification code characterizing the medical condition of the patient is determined and recorded (STEP 508). Use of such codes may ease standardization of pain management algorithms. The preferred standard codes are known as ICD-9 (or a variant thereof), which are based on the official version of the World Health Organization's 9th Revision, International Classification of Diseases. ICD-9 codes are designed for classification of morbidity and mortality information for statistical purposes, and for indexing of hospital records by disease and operations, for purposes of data storage and retrieval. Every U.S. hospital codes diagnoses and procedures in ICD-9 or a variant (such as ICD-9-CM, for "Clinical Modification").

Based on the patient's initial complaint and after review of the demographic and medical symptom information submitted by the patient, the PMA system proceeds to a diagnostic phase by selecting and presenting to the care provider one or more rule-based pain management algorithms of the type shown in FIGS. 4A–4C (STEP 510). The primary care provider may then select the most applicable pain management algorithm (STEP 512) (in the preferred embodiment, the discretion and judgment of the primary care provider are never overridden). For example, if the medical history of a patient indicates cancer is present, then the pain management algorithm shown in FIG. 4A may be presented.

Once a pain management algorithm is selected, the questions recorded in the rules of the pain management algorithm are posed to the patient (STEP 514). All questions and answers are recorded in the patient's file for later review (STEP 516). Again, responses may be gathered by presenting suitable graphical user interface screens to the patient and permitting the patient to fill in blank items, or by having a care provider ask questions orally and record oral answers.

Based upon the patient's responses to the pain management algorithm questions, the PMA system recommends a treatment plan (STEP 518). The primary care provider is then permitted to approve the treatment plan (STEP 520). If so, a prescription is prepared and printed, and a set of patient instructions is either printed or downloaded to a portable computer running the PMA II program (STEP 522). A record of the treatment plan and generated prescription and patient instructions is added to the patient's medical file (STEP 524). If the patient does not use a portable computer running the PMA II program, the interaction with the primary care provider is now complete and the patient is dismissed.

If the patient is not new (STEP 500), the PMA system verifies the patient's status and updates the patient complaint and current pain score. If the patient presents a new complaint (STEP 550), the system proceeds as with a new patient, and collects and enters information about the patient's basic complaint and medical symptoms into the patient database (STEP 504). If the complaint is the same as the previous complaint, the system verifies whether the symptoms have changed. If the symptoms have changed (STEP 552), a new diagnosis is required and the system proceeds as with a new complaint (STEP 504).

If the complaint and symptoms are the same as those from the prior visit, the system advances the therapy one step and selects a new treatment plan from the available options for the patient (STEP 554). For example, referring to FIG. 4A, if "Treatment b" is not effective initially, the treatment plan for the patient can be advanced to "Treatment c". Thereafter, the system continues at STEP 518. Accordingly, once the new treatment plan is approved (STEP 520), a new set of patient instructions and prescriptions are generated (STEP 522). The instructions are then either printed for the patient or downloaded on to the PMA II platform. A record of the new treatment plan and generated prescription and patient instructions is added to the patient's medical file (STEP 524).

If the patient is using portable computer running the PMA II program, the physician downloads the initial set of patient instructions to the computer. The purpose of this system is to minimize the pain and maximize the patient's productive time. The PMA II program uses an inductive learning function, which is able to gradually adapt its advice to suit the individual. Through reminder and registration functions, the PMA II program collects patient data such as general health, whether and when medication was taken, other physical or mentally stressing activities, and observed side effects from medication or activities. Through the use of inductive learning and case-based reasoning, new rules for the management of the particular type of pain are generated.

As long as the new rules do not violate the guidelines established by the primary care provider, they are implemented. Should a new rule violate these guidelines, an alarm instructs the patient to download the data to the clinic and receive new instructions. For example, a downloaded set of instructions for a patient may include the following data record:

| Drug | Dosage | Dosage Times | Conditions | Confirmation |
|---|---|---|---|---|
| Amitryptiliine | 1 tablet | 0700 | Take with | <empty> |
|  |  | 1200 | water | <empty> |
|  |  | 1700 |  | <empty> |

Of course, the instruction record may be more complex, to deal with "on demand" dosing, maximum daily dosing, drug interaction warnings, etc.

The portable computer would include a real-time clock. At intervals, the PMA II program monitors the clock by means of timer calls. When it is time to take a drug, the reminder function 104 (see FIG. 3) alerts the patient. For example, a message such as "take one Amitryptiliine with water now" may appear on the portable computer's display, and the portable computer may beep. The registration function 106 then prompts the patient to confirm, by means of a screen touch or keypad entry, that the patient has taken the drug. A corresponding data field is then updated. For example, the time of confirmation may be entered into a corresponding data field in the "Confirmation" column noted above. The PMA II program also has the ability to prompt the patient to honestly enter "off-schedule" dosing or changed dosing (i.e., too little or too much).

In some cases, the registration function 106 may ask about current health status. The questions posed to the patient are preferably specifically tailored to the known symptoms of the patient. For example, a patient may always be asked about a pain score, but be asked about dizziness, nausea, dry mouth, blurred vision, etc., only where such conditions are common side-effects of a particular drug. The patient's answers are stored in the portable computer in a situation database 108.

Periodically, such as at the end of each day, an inductive learning module 110 in the PMA II program automatically recalls the entries of the day from the situation database 108 and examines the conditions when the patient was feeling fine versus when the patient was in pain. The PMA II program then generates a rule or hypothesis about what constituted successful medication advice. A preferred method for generating such rules or hypotheses is to apply "case-based reasoning", a well-known inductive learning technique. A description of such methods is set forth in *"Case-Based Reasoning: Opportunities and Applications in Healthcare"* by Macura, Robert T. and Macura, Katarzyna, Artificial Intelligence In Medicine (Elsevier 1997) (see also references cited therein). The rule may be as simple as "pain is at minimum after administration of 1 tablet Amitryptiliine if taken with food". A proposed rule (e.g., amending the instruction of "take with water" to "take with food") is then tested by a rule validation module 112, which compares each new rule with guidelines established by the primary care provider (e.g., maximum daily dosage levels, etc.). If a hypothesis is found and validated, it is stored in the knowledge base 102 of the PMA II program. In many cases, after approximately two weeks, the knowledge base contains a large number of rules about how to advise the patient. If a new rule violates these guidelines, an alarm 114 instructs the patient to download the data to the clinic (e.g., by means of a modem) and receive new instructions.

The primary care provider can recall the patient data to examine how the patient reacted to a prescribed therapy. In addition, the primary care provider can evaluate patient compliance with a treatment plan, and evaluate adverse events.

In the preferred embodiment, the reminder function 104 and the learning module 110 are fully automatic. The situation database 108 contains the patient observations for the previous 60 days. The inductive learning module 110 includes a data preparation module and a database for typical and relevant cases derived from the situation database 108. The inductive learner discovers the most successful cases and constructs rules for the reminder system. The rule validation module 112 automatically validates all rules using limits and restrictions determined by the primary care provider. The final knowledge base 102 used by the reminder function 104 thus contains successful and proven rules for the individual. The system learns incrementally as long as the learning function is activated. Thus, the PMA II program is adaptive and as conditions change, the system identifies them and gradually amends the patients rules.

The invention may be implemented in hardware or software, or a combination of both. However, preferably, the invention is implemented in computer programs executing on programmable computers each comprising at least one processor, at least one data storage system (including volatile and non-volatile memory and/or storage elements), at least one input device, and at least one output device. Program code is applied to input data to perform the functions described herein and generate output information. The output information is applied to one or more output devices, in known fashion.

Each program is preferably implemented in a high level procedural or object oriented programming language to communicate with a computer system. However, the programs can be implemented in assembly or machine language, if desired. In any case, the language may be a compiled or interpreted language.

Each such computer program is preferably stored on a storage media or device (e.g., ROM or magnetic diskette) readable by a general or special purpose programmable computer, for configuring and operating the computer when the storage media or device is read by the computer to perform the procedures described herein. The inventive system may also be considered to be implemented as a computer-readable storage medium, configured with a computer program, where the storage medium so configured causes a computer to operate in a specific and predefined manner to perform the functions described herein.

A number of embodiments of the present invention have been described. Nevertheless, it will be understood that various modifications may be made without departing from the spirit and scope of the invention. Accordingly, other embodiments are within the scope of the following claims.

What is claimed is:

1. A computer-implemented method for generating a pain management treatment plan comprising the steps of:

(a) presenting from a computer to a care provider at least one rule-based pain management algorithm based on gathered medical symptom information for the patient and a pain score representing the patient's subjective ranking of the patient's pain;

(b) applying a rule-based algorithm selected by the care provider to ask the patient questions about pain characteristics of the patient;

(c) inputting responses from the patient to such questions into the computer;

(d) generating in the computer a treatment plan recommendation for the patient based on the responses;
(e) generating from the computer prescription information including a prescription and treatment instructions in accordance with the adopted treatment plan.

2. A computer program, residing on a computer-readable medium, for generating a pain management treatment plan, comprising instructions for causing a computer to:
   (a) present to a care provider at least one rule-based pain management algorithm based on gathered medical symptom information for the patient and a pain score representing the patient's subjective ranking of the patient's pain;
   (b) accept responses from the patient to questions from a rule-based algorithm selected by the care provider about pain characteristics of the patient;
   (c) generate a treatment plan recommendation for the patient based on the responses;
   (d) generate prescription information including a prescription and treatment instructions in accordance with the adopted treatment plan.

3. A method for pain management comprising the steps of:
   (a) gathering medical symptom information for the patient and inputting such medical symptom information into the computer;
   (b) obtaining a pain score from the patient representing the patient's subjective ranking of the patient's pain and inputting the pain score into the computer;
   (c) generating a treatment plan for the patient by the steps of:
      (1) presenting to a care provider at least one rule-based pain management algorithm based on the gathered medical symptom information and the pain score as an indicator of actual pain severity;
      (2) permitting a care provider to select one of the rule-based pain management algorithms;
      (3) applying the selected rule-based algorithm to ask the patient questions about pain characteristics of the patient;
      (4) inputting responses from the patient to such questions into the computer;
      (5) generating a treatment plan recommendation for the patient based on the responses;
   (d) permitting a care provider to adopt the treatment plan;
   (e) generating prescription information including a prescription and treatment instructions in accordance with the adopted treatment plan;
   (f) recording the adopted treatment plan and generated prescription information in the computer as a patient file.

4. The method of claim 3, further including the step of characterizing the patient with a preselected standard code and inputting such code into the computer.

5. The method of claim 4, wherein the preselected standard code is an ICD9 code.

6. The method of claims 1 or 3, further including the steps of:
   (a) downloading the treatment instructions to a patient computer;
   (b) prompting patient compliance with the downloaded treatment instructions;
   (c) recording in the patient computer patient compliance with each downloaded treatment instruction;
   (d) recording in the patient computer patient medical symptom information and a pain score.

7. The method of claim 6, further including the steps of:
   (a) evaluating the recorded patient medical symptom information and pain score;
   (b) generating a proposed change in a patient treatment plan based on such evaluation.

8. The method of claim 7, further including the steps of:
   (a) validating each proposed change in a patient treatment plan;
   (b) adopting each validated proposed change as part of a new patient treatment plan.

9. The method of claim 6, further including the step of:
   (a) communicating the recorded patient medical symptom information and pain score from the patient computer to the care provider.

10. A computer program, residing on a computer-readable medium, for pain management, comprising instructions for causing a computer to:
    (a) accept medical symptom information for the patient;
    (b) accept a pain score from the patient, where the pain score represents the patient's subjective ranking of the patient's pain;
    (c) generate a treatment plan for the patient by:
       (1) presenting to a care provider at least one rule-based pain management algorithm based on the gathered medical symptom information and the pain score as an indicator of actual pain severity;
       (2) permitting a care provider to select one of the rule-based pain management algorithms;
       (3) accepting responses from the patient to questions from the selected rule-based algorithm about pain characteristics of the patient;
       (4) generating a treatment plan recommendation for the patient based on the responses;
    (d) permit a care provider to adopt the treatment plan;
    (e) generate prescription information including a prescription and treatment instructions in accordance with the adopted treatment plan;
    (f) record the adopted treatment plan and generated prescription information in the computer as a patient file.

11. The computer program of claim 10, further including instructions for causing the computer to accept input of a preselected standard code characterizing the patient.

12. The computer program of claim 11, wherein the preselected standard code is an ICD9 code.

13. The computer program of claims 2 or 10, wherein the instructions permit the computer to download the treatment instructions to a patient computer, and further including a second computer program comprising instructions for causing the patient computer to:
    (a) prompt patient compliance with the downloaded treatment instructions;
    (b) record in the patient computer patient compliance with each downloaded treatment instruction;
    (c) record in the patient computer patient medical symptom information and a pain score.

14. The computer program of claim 13, wherein the second computer program further includes instructions for causing the patient computer to:
    (a) evaluate the recorded patient medical symptom information and pain score;
    (b) generate a proposed change in a patient treatment plan based on such evaluation.

15. The computer program of claim 14, wherein the second computer program further includes instructions for causing the patient computer to:
(a) validate each proposed change in a patient treatment plan;
(b) adopt each validated proposed change as part of a new patient treatment plan.

16. The computer program of claim 13, wherein the second computer program further includes instructions for causing the patient computer to:
(a) communicate the recorded patient medical symptom information and pain score from the patient computer to the care provider.

\* \* \* \* \*